(12) United States Patent
Duthie et al.

(10) Patent No.: US 8,753,868 B2
(45) Date of Patent: Jun. 17, 2014

(54) METHOD AND SYSTEM FOR SELECTIVE ISOLATION OF TARGET BIOLOGICAL MOLECULES IN A GENERAL PURPOSE SYSTEM

(75) Inventors: Robert Scott Duthie, Schenectady, NY (US); Wei-Cheng Tian, Clifton Park, NY (US); Tarun Khurana, Stanford, CA (US)

(73) Assignee: General Electric Company, Niskayuna, NY (US)

( * ) Notice: Subject to any disclaimer, the term of this patent is extended or adjusted under 35 U.S.C. 154(b) by 1191 days.

(21) Appl. No.: 12/185,680

(22) Filed: Aug. 4, 2008

(65) Prior Publication Data

US 2010/0029915 A1    Feb. 4, 2010

(51) Int. Cl.
*C12M 1/00*     (2006.01)
*G01N 27/26*    (2006.01)
*B01D 57/02*    (2006.01)
*G01N 27/447*   (2006.01)
*B01L 3/00*     (2006.01)

(52) U.S. Cl.
CPC .......... *G01N 27/447* (2013.01); *B01L 3/50273* (2013.01)
USPC .................. 435/283.1; 435/288.5; 435/288.6; 204/450; 204/600

(58) Field of Classification Search
None
See application file for complete search history.

(56) References Cited

U.S. PATENT DOCUMENTS

| | | | |
|---|---|---|---|
| 5,126,022 A * | 6/1992 | Soane et al. ................ 204/458 |
| 5,770,029 A * | 6/1998 | Nelson et al. .............. 204/604 |
| 5,808,043 A | 9/1998 | Duthie et al. |
| 5,876,934 A | 3/1999 | Duthie et al. |
| 6,129,828 A | 10/2000 | Sheldon, III et al. |
| 6,287,764 B1 | 9/2001 | Hildebrand et al. |
| 6,660,480 B2 | 12/2003 | Ramsey et al. |
| 7,138,254 B2 | 11/2006 | Jovanovich et al. |
| 7,160,423 B2 * | 1/2007 | Chien et al. ................ 204/453 |
| 7,320,754 B2 | 1/2008 | Carlsson et al. |
| 7,351,801 B2 | 4/2008 | Belew |
| 7,368,561 B2 | 5/2008 | Eriksson et al. |
| 7,385,040 B2 | 6/2008 | Johansson et al. |
| 7,423,070 B2 | 9/2008 | Larsson et al. |
| 7,423,124 B2 | 9/2008 | Belew et al. |
| 7,625,760 B2 * | 12/2009 | Kitaguchi et al. ............ 436/165 |
| 7,740,747 B2 * | 6/2010 | Tian et al. .................. 204/453 |
| 7,740,748 B2 * | 6/2010 | Tian et al. .................. 204/453 |
| 2001/0035351 A1 | 11/2001 | Simpson et al. |
| 2002/0040873 A1 | 4/2002 | Wahlberg et al. |
| 2007/0128629 A1 | 6/2007 | Hildebrand et al. |
| 2008/0003602 A1 | 1/2008 | Nelson et al. |

OTHER PUBLICATIONS

PCT Search Report and Written Opinion—Sep. 28, 2009.

(Continued)

*Primary Examiner* — Betty Forman
(74) *Attorney, Agent, or Firm* — Fletcher Yoder, P.C.

(57) ABSTRACT

Embodiments of the present techniques provide systems and methods for isolating particular classes of biological molecules, for example, proteins or nucleic acids, from mixtures of biological components. The methods use solutions that react with the biological molecules to enhance their adsorption by substrates, allowing contaminants to be washed away from the targeted molecules. Embodiments include automated systems that can be used to implement the technique with no or minimal intervention. Other embodiments include separation column technologies that may be used in the techniques.

8 Claims, 8 Drawing Sheets

(56) References Cited

OTHER PUBLICATIONS

Silas, M. J., et al., Concurrent mRNA and protein extraction from the same experimental sample using a commercially available column-based RNA preparation Kit, BioTechniques, vol. 40, No. 1, Jan. 2006, pp. 54-55.

Tolosa, Jorge M., et al., Column-based method to simultaneously extract DNA, RNA, and proteins from the same sample, BioTechniques, vol. 43, No. 6, Dec. 2007, pp. 799-804.

* cited by examiner

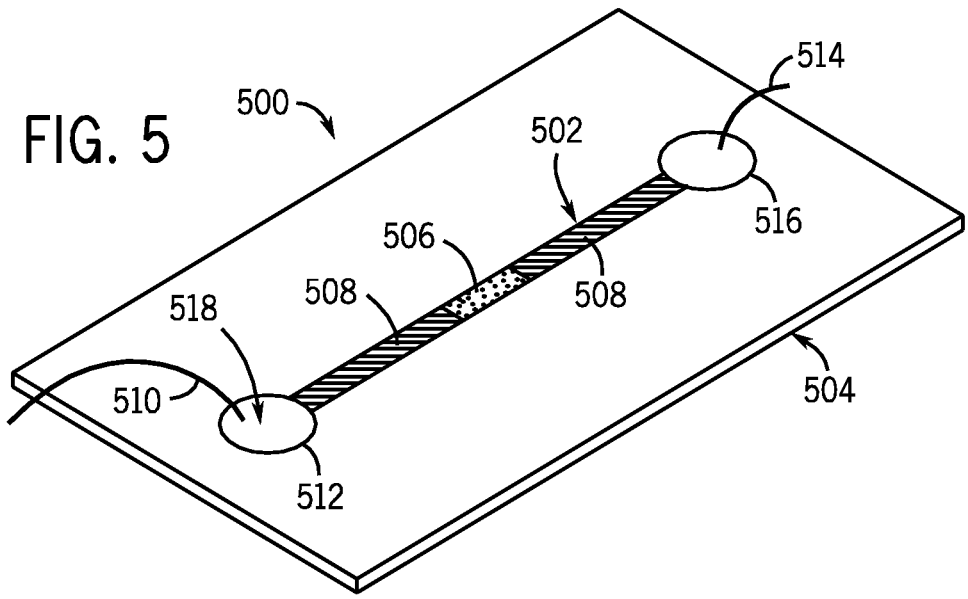
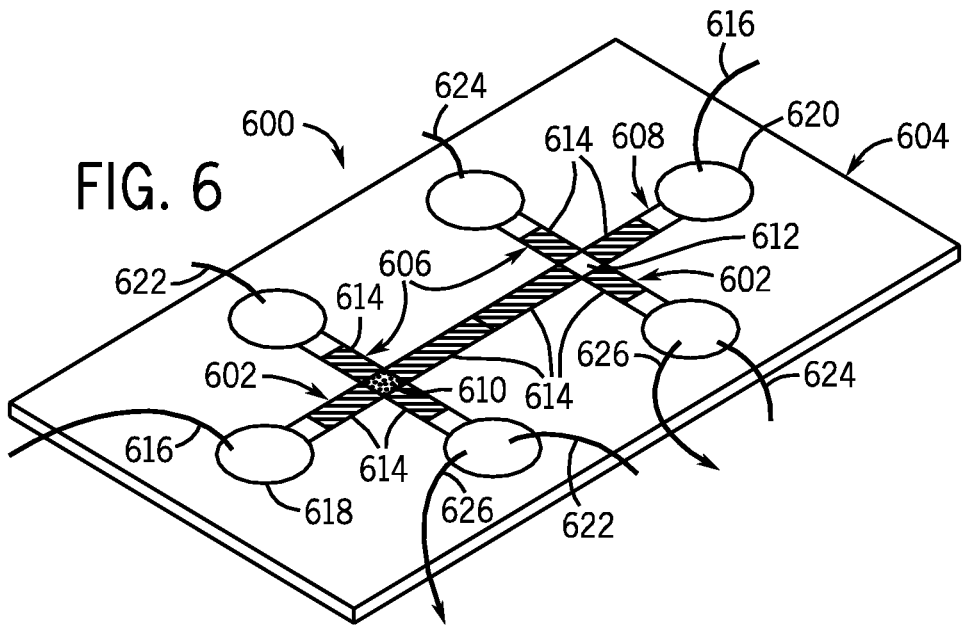

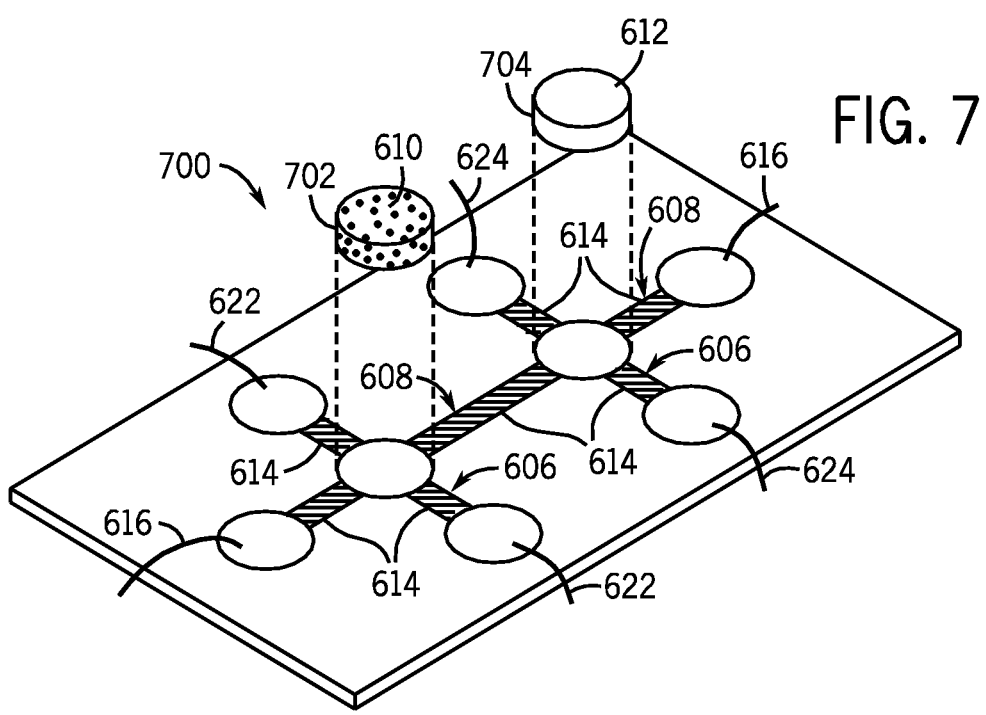

METHOD AND SYSTEM FOR SELECTIVE ISOLATION OF TARGET BIOLOGICAL MOLECULES IN A GENERAL PURPOSE SYSTEM

FIELD OF THE INVENTION

The techniques disclosed relate generally to systems and methods for isolating biological molecules from solutions containing mixtures of biological molecules. Specifically, for example, the techniques allow the selective isolation of proteins or nucleic acids from mixtures of biological components.

BACKGROUND

The purification of molecules of biological origin (biomolecules), such as proteins and nucleic acids from mixtures has generally been based on laboratory techniques developed for research operations. For example, techniques developed for laboratory operations in chemistry, microbiology, biochemistry, or immunology may currently be used for isolation and purification of biomolecules. These techniques may involve numerous steps, including, for example, lysing cells in a solution to release biological molecules, centrifugation to pellet material or move fluid through a solid-phase capture structure, and adding a solution to a solid phase capture structure to release adsorbed purified biomolecules from said structure. The solution of resuspended biomolecules may then, for example, be used in downstream applications as diverse as immunoassay, PCR, or mass spectrometry.

While effective, these purification procedures may be very time and labor intensive. Further, the various steps may generally be specific to the particular molecules being analyzed. Accordingly, the techniques may be impractical for use in clinical or field applications.

BRIEF DESCRIPTION

An embodiment of the present techniques provides an automated system for isolating biological molecules from a sample. The system includes a substrate having at least one universal surface configured to adsorb a plurality of types of biological molecules. The system also includes an automated fluid-control system configured to contact a sample with one or more solutions adapted to act on one or more of the types of biological molecules from the sample and a processing system configured to automatically determine which of the solutions the fluid-control system should contact with the sample based at least in part on the type of biological molecules to be isolated.

An embodiment of the present techniques provides a method for isolating biological molecules from a sample. The method includes the act of automatically selecting a solution based at least in part on the solution's specificity for binding one or more types of biological molecule(s) of interest. The solution is automatically combined with a sample comprising the one or more types of biological molecule(s) of interest. The combined solution is automatically placed in contact with a universal substrate configured to reversibly adsorb a plurality of types of biological molecules including the one or more types of biological molecule of interest.

Another embodiment provides a kit for isolating biological molecules from a sample. The kit includes a first solution configured to facilitate the isolation of proteins from the sample and a second solution configured to facilitate the isolation of nucleic acids from the sample. The kit also includes a universal substrate configured to reversibly adsorb a biological molecule that has been reacted with at least one of the first solution or the second solution.

A further embodiment provides a micro-fluidic device for isolating biological molecules from mixtures. The device includes a base material, a main channel formed in the base material, and a cross channel formed in the base material. The cross channel intersects the main channel and a substrate is fluidically coupled to both the main channel and the cross channel. Both the main channel and the cross channel have electrophoresis connections on either side of the substrate disposed within the channels.

DRAWINGS

These and other features, aspects, and advantages of the present invention will become better understood when the following detailed description is read with reference to the accompanying drawings in which like characters represent like parts throughout the drawings, wherein:

FIG. 5 is a perspective view of a micro-fluidic device that may use both solvent flow and electrophoresis to isolate biomolecules, in accordance with an embodiment;

FIG. 6 is a perspective view of a micro-fluidic device that may use both solvent flow and electrophoresis techniques to isolate biomolecules, in accordance with an embodiment;

FIG. 7 is a perspective view of a another micro-fluidic device that may use both solvent flow and electrophoresis techniques to isolate a target biomolecule, in accordance with an embodiment;

DETAILED DESCRIPTION

Figure 1:
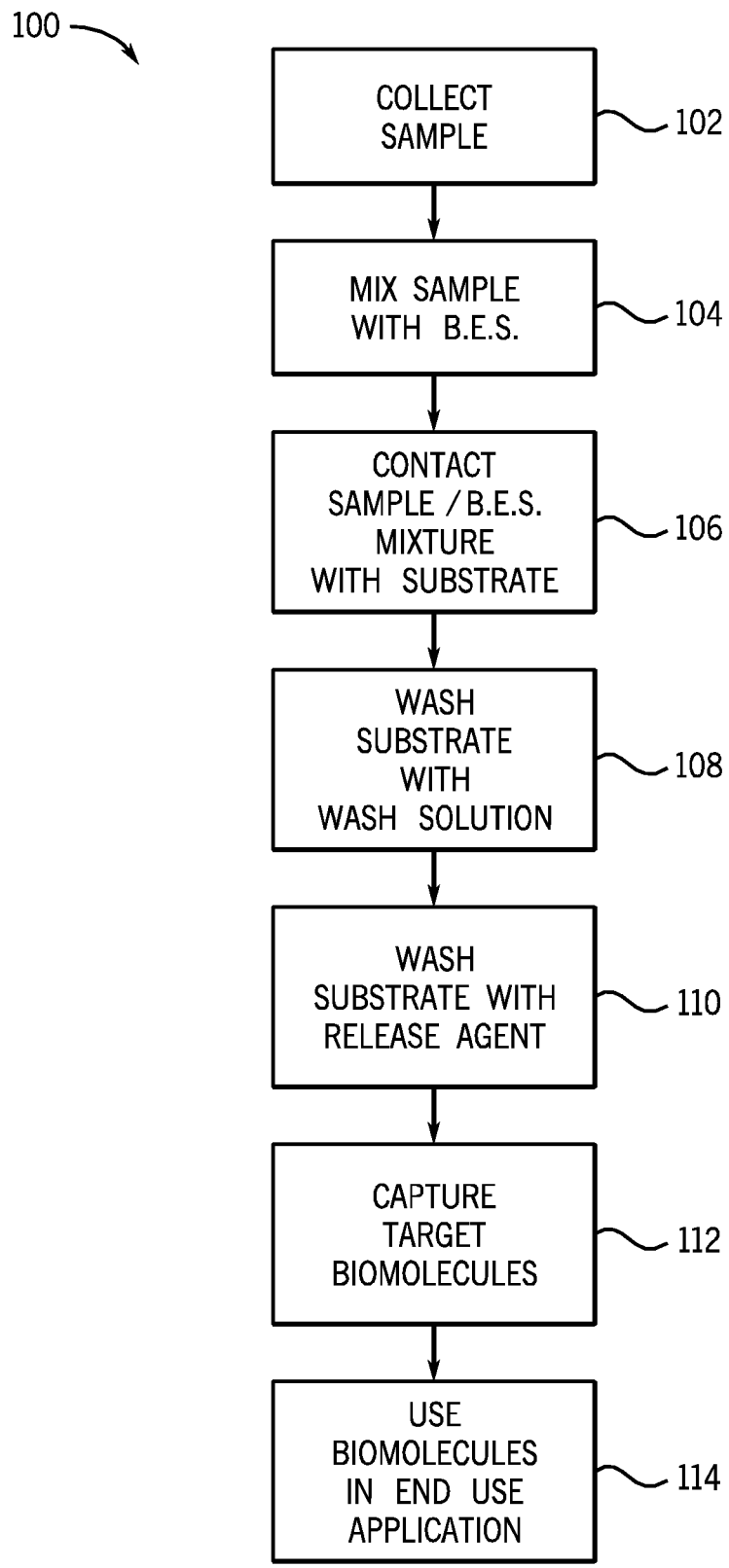
FIG. 1 is a block diagram of a general analysis technique for the isolation of biomolecules, in accordance with embodiments.

The techniques discussed below provide simple and adaptable procedures for the isolation of target biomolecules from a source solution. The target biomolecules may include, for example, proteins, nucleic acids, viral RNA, and cellular DNA, among others, and may be contained within cellular or nuclear membranes. The procedures may be implemented in a single, easily operated analysis unit which may be fully automated in certain embodiments. Such a unit may be configured to provide fast results in a field setting, for example, when the detection of biological agents, e.g., infectious agents, is needed. The source solution containing the target biomolecules may include, for example, a solution containing a mixture of biomolecules, the rinse from a cotton swab, cells, virus particles, or other sources of biomolecules.

Implementation of the techniques does not require the use of multiple individual preparation steps, but merely the selection of an appropriate solution, e.g., a binding and extraction solution (BES), that is specific to the biomolecules desired. The BES may perform the necessary reactive steps for isolation of the target biomolecules, for example, lysing cellular and nuclear membranes for extraction of nuclear DNA. Further, the BES may react with the target biomolecules to enhance their adsorption onto the universal substrate.

Generally, the source solution may be introduced into the analysis unit, where it may be combined with the appropriate binding and extraction solution. After a reaction period, the reaction mixture may be placed on a column containing a universal substrate. The target biomolecules may be reversibly adsorbed by the substrate, while other components are eluted out of the column. The column may then be rinsed with a wash solution to remove any remaining contaminants. Finally, a release solution containing a release agent may be applied to reverse the adsorption, allowing the target biomolecules to elute from the column.

The purified target biomolecules may be detected and analyzed, for example, using spectroscopic or electrochemical techniques. Such techniques may be used to provide information about the biomolecules, as well as assisting in the isolation of pure fractions. Further, the isolated biomolecules may be used in procedures downstream of the isolation for further analysis, including, for example, amplification, sequence analysis, comparative analysis of genetic components with the proteins they generate, analysis on etched chip microprobes, among other applications.

The separation columns that contain the substrate may be formed from tubing or may be micro-fluidic devices, formed from channels made in a base material. The reacted solution may be eluted through the column using pressure from a pump or may be eluted using electrophoresis, or a combination thereof. Further, the micro-fluidic devices may have cross channels formed in the base material that intersect with the main channel. Different substrates, targeting different biomolecules, may be incorporated into the device, with each different substrate located at the intersection of the main channel with a cross channel. This configuration may facilitate the simultaneous or overlapping separation of the biomolecules from the individual substrates, with different biomolecules eluting from different cross channels.

The procedures discussed above may also be implemented on more complex units in a clinical or laboratory setting. Such units may include automated injection devices configured to facilitate the analysis of large numbers of solutions. Further, the units may include automated collection devices to facilitate collecting sample aliquots for further analysis.

General Procedure for Purification of Target Biomolecules

A general method 100 that may be used in an embodiment of the present techniques for the isolation of target biomolecules from a solution is shown in the block diagram of FIG. 1. The method 100 begins in block 102 with the sample collection. Collection of the sample may include, for example, any number of steps designed to collect and prepare a sample in a laboratory or field setting, as discussed in further detail with respect to FIG. 9, below.

The sample may be mixed with the appropriate binding and extraction solution (BES) for the target biomolecules, as shown in block 104. The BES may react with the target biomolecules in the sample solution to prepare them for adsorption to the universal substrate. Further, the BES may extract the target biomolecules from membranes in cells, bacteria, and the like, by lysing the membranes encasing the target biomolecules. Examples of BESs that may be used in embodiments of the present techniques are shown in Table 1, below. These BESs are labeled A through E and each targets a specific type of biomolecules.

For example, BES A may be useful for the extraction of non-nuclear DNA, for example, plasmid or expression vector DNA from bacterial cells. The solution in certain described embodiments is a base and a buffer. In such embodiments, the base (e.g., sodium hydroxide) is used to lyse the outer cell membrane and extract the components contained within the cell. These components may include, for example, plasmids or other vector DNAs. A buffering agent (e.g., the HCl salt of 2-amino-2-hydroxymethyl-propane-1,3-diol (Tris-HCL)) modulates the effect of the base and promotes the selective binding of the extracted plasma DNA to a substrate.

Bases which may be used to form BES A include, for example, KOH, $Na_3PO_4$, $NH_2OH$, or LiOH, among others. In an embodiment, for example, the concentration range of the base used, e.g., NaOH, may be between about 0.01 and about 1.00 normal. In another embodiment, the concentration of the base may be between about 0.1 and about 0.2 normal. Other buffering agents may be used in embodiments of the present techniques, including, for example, carbonate buffers, citrate buffers, acetate buffers, bis-tris buffers, pyrophosphate buffers, phosphate buffers, HEPES buffers, tricine buffers, or any other organic or inorganic buffers. In certain embodiments, these buffers may be used in concentration ranges of between about 0.01 and about 5.0 molar. In other embodiments, the concentrations may range from about 0.1 to about 1.0 molar.

TABLE 1

Binding and Extraction Solutions

| BES | Description | Composition | Target |
|---|---|---|---|
| A | Buffered Base ±[1] Detergents | 0.1-0.2 N NaOH<br>0.1-1.0 M Tris HCl (pH 12)<br>±0.5% Tween 20 | Non-nuclear DNA |
| B | Buffered Base ± Stabilizer | 0.1-0.2 N $Na_xPO_4$<br>0.1-1.0 M Tris HCl (pH 9)<br>±20% Glycerol | Proteins |
| $C_1$ | Buffered Base +[2] Acetate Salts | 0.1-0.2 N NaOH<br>0.1-1.0 M Tris HCl<br>5.8 M Acetate pH 7-8 | Nuclear DNA |
| $C_2$ | Buffered Chaotrope ± Detergents | 3.5-7.0 M Guanidine HCl<br>0.1-1.0 M Tris HCl pH 4-7<br>0.5% Nonidet P40 | Nuclear DNA |
| $D_1$ | Buffered Chaotrope ± Detergents | 0.1-3.5 M Guanidine HCl<br>0.05 M Tris HCl (pH 6-7)<br>0.5% Nonidet P40 | Total RNA |

TABLE 1-continued

Binding and Extraction Solutions

| BES | Description | Composition | Target |
|---|---|---|---|
| $D_2$ | Buffered Chaotrope + Denaturing Solvation Modulators ± Detergents | 3.5-7.0 M Guanidine HCl<br>0.05 M Tris HCl (pH 6-7)<br>10-50% DMF or DMSO<br>0.5% Nonidet P40 | Total Nucleic Acid |
| $D_3$ | Buffered Detergent + Salts ± Reducing Agents | 0.5% Nonidet P40<br>0.01 M Tris HCl (pH 6-7)<br>0.015 M MgCl$_2$ and NaCl<br>0.001 M Dithiothreitol | Total Nucleic Acid |
| E | Buffered Chaotrope | 5.0 M Guanidine Isothiocyanate<br>0.5 M Tris Acetate pH 6.6 | DNA Fragments |

[1]"±" indicates that the solution may optionally contain the following component
[2]"+" indicates that the solution does contain the following component The final pH of BES A may be between about 10 and about 14 pH log units, or about 12.0. In some embodiments, a non-ionic surfactant type detergent may extend the range of cell types that may be extracted. Such detergents may include, for example, the Triton X series of detergents (available from Dow Chemical of Midland, Mich.), the Tween series of detergents (available from Croda International PLC of East Yorkshire, UK), and Igepal CA-630 (available from Sigma-Aldrich corporation of St. Louis, Mo.). Any number of other detergents that have essentially the same characteristics as the non-ionic surfactants listed above may be used in other embodiments. In embodiments where a detergent may be used, the detergent may be in a concentration range of about 0.1 percent to about 5 percent, or at a concentration of about 0.5 percent.

Another BES that may be used in an embodiment is shown as BES B in Table 1. BES B may be used for the extraction and isolation of proteins, for example, expressed proteins from prokaryotic, eukaryotic, or viral sources. BES B is similar to BES A in that it may consist of a base and a buffer. However, BES B differs in the final pH and in the presence of an optional stabilizer, e.g., glycerol. As with BES A, BES B includes a base, e.g., alkaline Na$_3$PO$_4$, which may lyse cell walls or membranes, or the coat proteins of RNA viruses and, thus, extract biological molecules from the cellular or viral components of the sample.

BES B promotes the selective binding of an extracted protein to a substrate support. The presence of stabilizer (e.g., glycerol, glycerin, and the like) modulates the base and may inhibit other effects, for example, irreversible DNA denaturation, hydrolysis, or proteolysis. The bases that may be used in BES B are essentially the same as those discussed with respect to BES A and may be used at around the same concentration levels as BES A. Similarly, the buffering agents would also be the same as described for BES A, with the exception that the pH range may be between about 8.0 and about 12.0 pH units or at about 9.0 pH units. In embodiments, the concentration of the glycerol in the solution may range from about 1 percent to about 50 percent by weight, or about 20 percent.

The third general type of BESs in Table 1, labeled C, is particularly useful for the extraction and isolation of large DNA molecules, e.g., genomic DNA, from any number of cell types, including, for example, prokaryotic cells, eukaryotic cells or from infecting viruses or other parasitic agents found in the sample. BES C has two different formulations that may be used in embodiments of the present techniques, labeled $C_1$ and $C_2$, as discussed below.

BES $C_1$ is similar to BES A and B in that it may simply be a combination of base and a buffer. However, BES $C_1$ may also include an additional component to modulate the adhesion of the target biomolecules to the substrate. For example, in embodiments, the additional modulator may consist of acetate salts with a pH of between about 7.0 and about 9.0. The acetate salts may be used in a concentration range between about 1 to about 7 molar (M), or about 6 M. As with BES A and B, the base in BES C facilitates the lysis of cell walls or membranes and dissociates the target biomolecule from any interactions with other extracted ingredients. The base, in combination with the acetate salts may condition large DNA molecules (e.g., genomic DNA) to be reversibly adsorbed by the substrate. As is true for Solutions A and B, the base used in Solution C could include, but is not limited to, NaOH, KOH, Na$_3$PO$_4$, NH$_2$OH and LiOH. In embodiments, the concentration range of the base may be between about 0.01 N and about 1.00 normal (N), or may be between about 0.1 N and about 0.2 N. The same buffering agents described for BES A and B above, may be used in the same concentration ranges in BES $C_1$.

In another embodiment of BES C, labeled $C_2$ in Table 1, a high concentration of a chaotrope may be substituted for the base and may be used in combination with a buffer, e-g. Tris-HCL, to obtain large genomic DNAs. A chaotrope, or chaotropic agent, may disrupt the intermolecular forces, e.g., hydrogen bonds, Van der Waals forces, hydrophobic effects, and the like, binding DNA molecules together, and to other molecules, enabling the DNA molecules to be more easily extracted from mixtures. In certain embodiments, for example, guanidine HCl may be used as the chaotrope. However, the chaotrope is not limited to guanidine HCl, and in other embodiments, any number of chaotropic agents having similar function (such as guanidine isothiocyanate, urea, or lithium perchlorate, among others) may be used. Embodiments of BES $C_2$, may include guanidine HCl in a concentration range of between about 3.5 M and about 7.0 M. The buffer may be the same as for BES A and B and may be used in the same concentration ranges. In embodiments, the pH may be in a range of about 4.0 to about 7.0 pH log units. In this pH range and with the assistance of a detergent, e.g., Igepal CA-630, BES $C_2$ may lyse the cell walls and condition large DNA molecules for binding to the substrate. The detergents that may be used and the concentration ranges, may be the same as for BES A, described above.

In contrast to the BES C solutions, which target large DNA molecules, BES $D_1$, $D_2$, and $D_3$, more generally, target nucleic acids, for example, DNA and RNA, with the concentration of the components used to control selectivity. For example, BES $D_1$ may include a lower concentration of a chaotrope than in BES $D_2$. BES $D_1$ may facilitate the isolation of total RNA, including, for example, ribosomal, messenger, transfer and viral RNA species. The chaotrope may be chosen as discussed with respect to BES $C_2$, above. In embodiments, the concentration of a chaotrope in BES $D_1$ may range from about 0.1 M to about 3.5 M. In addition to the chaotrope, BES D1 may also include a buffer, e.g., Tris-HCl, and a detergent, e.g., Igepal CA-630. The buffers and detergents that may be used include those discussed with respect to BES A, above. In embodiments, the concentration of the buffers in BES $D_1$ may range from about 0.01 M to about 0.1 M, or about 0.05 M. In embodiments, the pH may be adjusted to be between about 5.0 to about 7.5 pH log units, or between about 6 and about 7 pH log units.

BES D type solutions may also be used to separate all of the nucleic acids from the sample solution. For example, as shown for BES $D_2$ in Table 1, a solution may include a higher concentration of chaotrope and may be supplemented with a denaturing solvation modifier, such as dimethyl formamide (DMF) or dimethyl sulfoxide (DMSO). This combination may allow BES $D_2$ to facilitate the isolation of substantially all of the nucleic acids from the sample. Total nucleic acid may include total RNA, genomic and other DNAs including those of viral origin. The chaotrope may be selected as discussed with respect to BES $C_2$, above. The concentration of the chaotrope may range from about 3.5 M to about 7.0 M. The concentration of the denaturing solvent, e.g., DMF or DMSO, may range between about 10% and about 50% by volume. The concentration for the buffer may range from about 0.01 M to 0.1 M, or about 0.05 M. The pH range of the final mixture before application to the sample may range from about 5.0 to about 7.5 pH log units, or from about 6.0 to about 7.0 log units.

Another embodiment that may be useful for isolating all of the nucleic acids from a sample is shown as BES $D_3$. BES $D_3$ may consist of a detergent, a buffer, salts, and a reducing agent. Detergents that may be used in embodiments, e.g., Igepal CA-630, are as discussed with respect to BES A, above. In embodiments, the concentration range for the detergent may be from about 0.1 to about 5.0%, or about 0.5%. Salts that may be used in embodiments include, for example, MgCl, NaCl, and the like. The concentration range of the salts may range from about 0.001 M to about 1.0 M, or about 0.015 M. The same buffers discussed with respect to BES A, e.g., tris-HCl, may be used in embodiments. The concentration for the buffer may range from about 0.001 M to about 1.0 M, or about 0.01 M. In an embodiment, dithiothreitol (DTT) may be used as the reducing agent. However, the choice of the reducing agent is not limited to DTT. For example, any number of organic or inorganic reducing agents may be selected, including dithioerythritol (DTE), diborane, sodium dithionite, and the like, depending on the reduction potential of the reagent. The concentration of the reducing agent may range from about 0.0001 M to about 0.1 M, or about 0.001 M. The concentration of the reducing agent may be adjusted based on the reducing potential in order to keep the overall activity similar.

The final entry in Table 1, BES E, may also be used for isolating fragments of nucleic acids from sample solutions, for example, PCR, cDNA, and sequencing fragments, among others. In embodiments, BES E may consist of a chaotrope and a buffer. For example, in an embodiment, BES E may use the chaotrope guanidine isothiocyanate in combination with Tris-acetate. Other chaotropes, as discussed with respect to BES $C_2$, above, may also be used. The concentration of the chaotrope may be between about 4.0 M and about 7.0 M. The buffering agent may be as discussed with respect to BES A, with a concentration between about 0.2 M and about 1.0 M. In embodiments, the pH range may range from about 4.0 to about 7.0 pH log units, or about 5.5 pH log units. In one embodiment the concentration of the chaotrope, e.g., guanidine isothiocyanate may be about 5.0 M and the concentration of the buffering agent may be about 0.5 M. In this configuration, the chaotrope may condition the target nucleic acids for selective binding to the substrate.

In addition to the BESs discussed above, other BESs may be used to isolate other types of biomolecules. For example, a BES that is specific to polysaccharides may be used in addition to the solutions shown above. In this BES, an aqueous acid, for example, HCl (aq) or $H_2SO_4$ (aq) may be used to hydrolyze the polysaccharide and prepare it for adsorption by the substrate.

After the sample solution has been mixed with the BES, the mixed solution may then be placed in contact (block 106) with a substrate. The substrate may reversibly adsorb the target biomolecules after their reaction with the BES. Substrates that may be used in embodiments of the present techniques include, for example, glass fibers, glass fiber filters, silica gel membranes, polysaccharide based porous sheets, anion exchange resins, charged nylons, diazotized membranes, and other suitable materials. One of ordinary skill in the art will recognize that these materials may include any substrate capable of weakly associating with a charged anion, so as to allow the charged anion to be removed without damage.

After the substrate has reversibly adsorbed the target biomolecules, the substrate may be washed (block 108) by a reagent to remove the remaining traces of the BES and any contaminating molecules from the support. The wash reagent may also condition the substrate in preparation for the subsequent elution of the purified product and, further, to purify and condition the target biomolecules. The wash reagent may include, for example, an alcohol solution, e.g., about 80% ethanol by volume, and a diluent/modifier, e.g., water, TE buffer (tris with ethylenediaminetetraacetic acid (EDTA)), or glycerol. The alcohol may facilitate the dehydration of the support prior to elution, which may increase the efficiency of the elution step and reduce the total volume of the eluate. This reduction in the total volume of the eluate may, for example, ease the analysis of the final product. The wash reagent may also include surface wetting agents, such as glycerol, which may prevent over-drying of bound target biomolecules. The surface wetting agents may reduce hydrophobic interactions between the substrate and the target biomolecules which could lead to degradation of the target biomolecules upon elution. The wash reagent may include about 70 to about 100% alcohol, by-volume in water or about 80% alcohol in water. Alcohols that may be used include, for example, methanol, propanol, or butanol, among others. Surface wetting agents that may be used in embodiments may include, for example, glycerin and silicone, among others. In an embodiment, the wash reagent may include about 80% ethanol and about 20% glycerol.

After the wash reagent has been used to remove contaminants and any residual BES from the substrate, the substrate may be treated (block 110) with a release agent. The release agent may be pure water, although, in other embodiments, additives may be used to enhance the utility of the released biomolecules. For example, if a purified nucleic acid is intended to be used in an enzymatic reaction, the release agent may be supplemented with buffers, for example, 2-amino-2-hydroxymethyl-propane-1,3-diol (Tris), in order to more readily support the next operation. In another example, the release agent may include a dye so that the eluted product can be immediately applied to a sequencer. Any number of other compounds may be added to the release agent to enhance the downstream use of the targeted biomolecules in further processes. For example, a release agent may include both a dye and a relative low concentration of alcohol, e.g., 60% or less, to aid in the concentration and loading of otherwise dilute samples onto a sequencer.

After treatment of the substrate with the release agent in block 110, the released target biomolecules may be captured for further processing, as shown in block 112. For example, in an embodiment, the biomolecules may be captured by sequentially capturing aliquots of the eluting solution as the wash reagent is flowed across the substrate. In another embodiment, a detector may be used to detect the presence of the target biomolecules and automatically collect aliquots containing the target biomolecules.

After the target biomolecules have been captured, either manually or under the control of an automated system, they may be used in other applications as shown in block 114. Potential applications are discussed in detail with respect to FIG. 9, below.

A Portable Analyzer for Isolating Biomolecules

Figure 2:
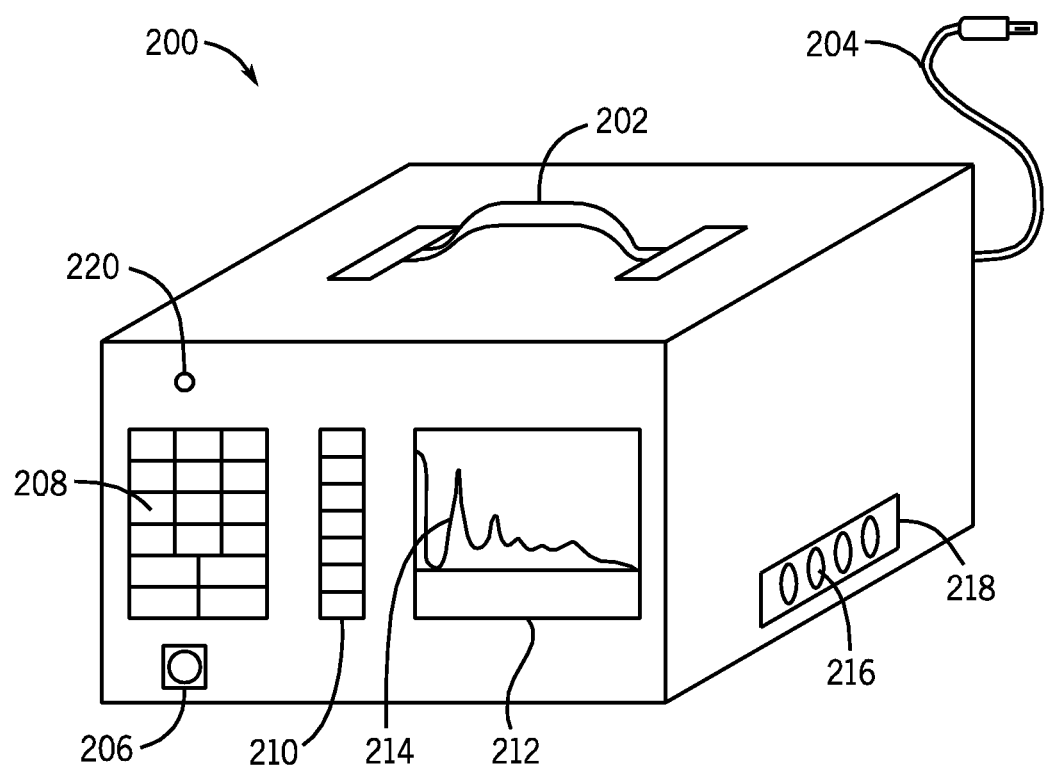
FIG. 2 is a perspective view of an automated analyzer for the isolation of a biomolecules, in accordance with an embodiment.

FIG. 2 shows a perspective view of a portable analyzer 200 that may be used to implement the techniques discussed with respect to FIG. 1. The portable analyzer 200 is a small unit for field analysis and may be carried to the point of use by a handle 202. The power for the portable analyzer 200 may be provided by any number of different techniques, for example, a car cigarette lighter plug 204. Any number of other techniques may be used to power the portable analyzer 200, including, for example, an adapter to allow the portable analyzer to be plugged into a wall socket or to be connected to a battery or to any other suitable power source.

The portable analyzer 200 may also have a number of controls for the entry of parameters and control of the analysis of the target's biological molecules. Such controls may include, for example, a power switch 206, a key pad for data entry 208, and programmable keys 210 that allow the entry of control parameters into the portable analyzer 200. In embodiments, the programmable keys 210 could be used in conjunction with the display 212 to show selections that may correspond to each of the programmable keys 210. The display 212 may also display analysis results 214 from a detector located within the portable analyzer 200.

Depending on the detectors used in embodiments, the portable analyzer 200 may display any number of analysis results 214, for example, the UV spectrum of the eluate from a column, the fluorescence spectrum of the eluate from a column, the refractive index of eluate from a column, or any number of other analysis results. The portable analyzer 200 may also allow for the collection of aliquots eluted from the column or columns in sample vials 216. The sample vials 216 may be accessible from the outside of the portable analyzer 200, for example, by sliding a cover 218 aside to reach the sample vials 216. One of ordinary skill in the art will recognize that any number of disposable or reusable containers may be used for the sample vials 216, including test tubes, injection vials, screw top vials, snap top vials, or any other suitable container. Once the sample is collected, the sample vials 216 may then be taken out of the portable analyzer 200, sealed, and shipped to a laboratory for further analysis.

Introduction of a sample into the portable analyzer 200 may be performed by any number of techniques. For example, the portable analyzer 200 may have a sample injection port 220 configured to allow a syringe or a syringe with an attached syringe filter to be connected to the portable analyzer 200. The portable analyzer 200 may represent one embodiment of an automated analyzer 300, as discussed with respect to FIG. 3, below.

An Automated Analyzer for Isolating Target Biomolecules

Figure 3:
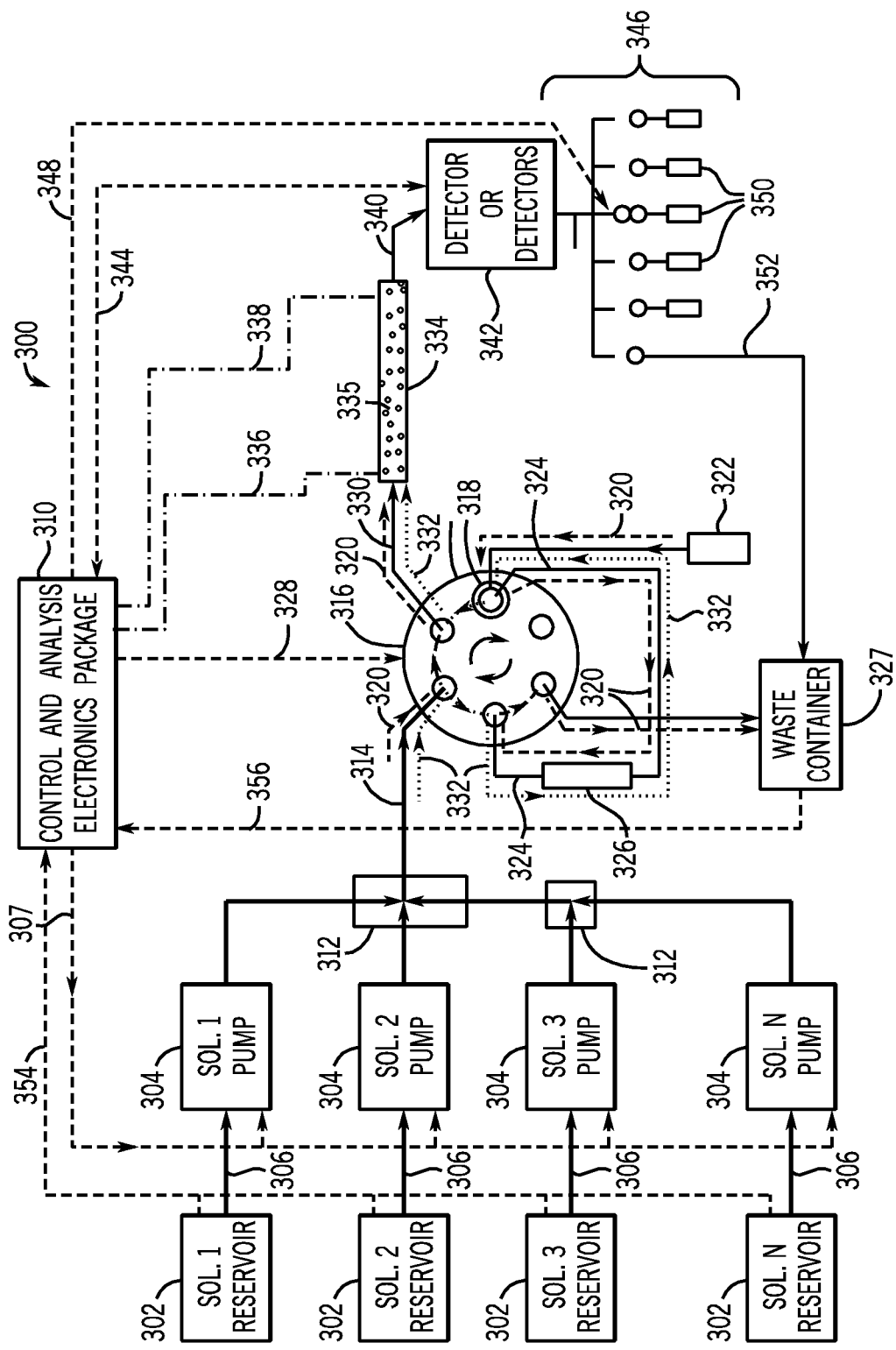
FIG. 3 is a block diagram of an automated analyzer for analyzing and isolating biomolecules, in accordance with an embodiment.

The components that may be used to make an exemplary automated analyzer 300 may be illustrated by the block diagram shown in FIG. 3. One of ordinary skill in the art will recognize that each block or component may include vessels, mechanical parts, electrical parts, or software, as needed to implement the labeled function. The automated analyzer 300 may have one or more solution reservoir containers 302 that may be used to hold the BESs, wash solution, and release agent discussed with respect to FIG. 1. Each solution reservoir 302 may be coupled to a solution pump 304 by a tubing line 306 connecting the solution reservoir 302 to the input of the solution pump 304. The operation of each individual solution pump 304 may be controlled by a control and power line 307 coming from a control and analysis electronics package (CAEP) 310. CAEP 310 may activate each solvent pump 304 individually or may activate any number of the solvent pumps 304 simultaneously.

The CAEP 310 may include any number of components necessary to power, analyze, or control any part of the analyzer 300. Such individual components may include, for example: a processor for the processing of machine readable instructions; memory for the storage of machine readable instructions, collected data, and user entries; a drive unit configured to operate the display 212 (as discussed with reference to FIG. 2); an input unit configured to accept data entry from the key pad 208 or the programmable keys 210; a high voltage power supply for powering an electrophoresis elution; or any number of other components needed to operate the unit. Further, the CAEP 310 may be assembled using existing electronic units, for example, those used for the control of liquid chromatography systems, and electrophoresis systems, among others. The CAEP 310 may also be specifically designed for the automated analyzer. One of ordinary skill in the art will recognize that a specifically designed unit may provide a smaller size, but assembling the CAEP 310 from pre-existing units may be done at a lower cost.

When powered by the CAEP 310, any individual pump 304 may convey the associated solution from the solution reservoir 302 through a tubing line 308 to a mixing manifold 312. The mixing manifold 312 may include forward flow valves configured to prevent the backflow of elution from any one solution pump 304 to any other solution pump 304. In a more complex configuration, the mixing manifold 312 may include a mixing chamber, for example, for mixing solutions from more than one solution pump 304. From the mixing manifold a solution may be conveyed through a tubing line 314 to a six-way sample valve 316.

The six-way sample valve 316 allows solutions to flow through a number of different ports 318 through two primary valve positions. In the first valve position the flow of solution is indicated by the dashed lines labeled 320. In this position, a sample injected through an injection port 322 may flow through the six-way valve 316 and be conveyed by a tubing line 324 through a reaction mixing tube 326. From the reaction mixing tube 326, the sample is conveyed back through the six-way valve 316 to a waste container 327, where any overflow from the injection, or any other waste solution, may be discarded. The reaction mixing tube 326 may include any number of different configurations. For example, in an embodiment, the reaction mixing tube 326 may merely be a widening in the tubing line 324 connecting the reaction mixing tube 326 to the ports 318 on the six-way valve 316. In other configurations the reaction mixing tube 326 may be more complex, for example, a separate reactor that includes a mixer or other unit designed to enhance the mixing of a sample solution with a BES. After the user has injected a sample through the injection port 322, the position of the six-way valve 316 may be changed to the second position by activation of a solenoid through a control line 328 from the CAEP 310.

In the second position, the flow of solutions to, and through, the six-way valve 316 is indicated by the dotted lines labeled 332. In this position, the six-way valve 316 connects the tubing line 314 from the mixing manifold 312 to tubing line 324, allowing solution from a solution pump 304 to be forced into the reaction mixing tube 326. From the reaction mixing tube 326, the solution flows through the six-way valve 316 and into a tubing line 330 where the reacted solution may flow into the separation column 334. The separation column 334 may contain a substrate 335, configured to reversibly adsorb a target biomolecule as discussed below.

Materials that may be used as the substrate 335 in the separation column 334 were discussed with respect to FIG. 1 above. Various column configurations which may be used as separation column 334 are discussed in detail with respect to FIGS. 4-7, below. The separation column 334 may use the flowing solution, as provided by a pump 304, to elute materials from the substrate 335 in the separation column 334 or may use an electrophoresis elution in addition to or in place of the pressure elution. If electrophoresis is used to elute materials across the separation column 334, a ground line 336 may be connected to one side of the separation column 334 and a high voltage line 338 may be connected to the opposite end of the separation column 334. The ground line 336 and the high voltage line 338 may be connected to a power supply in the CAEP 310 which may control the application of the elution current to the separation column 334.

The separation column 334 may be housed in a disposable, interchangeable cartridge to allow easy replacement. The use of such a cartridge may make the configuration of the automated analyzer 300 easier, allowing different materials or column configurations to be used for specific applications. The cartridge may have an identification component to show what type of biomolecules the specific substrate or configuration is designed to target. The identification component may be a bar code printed on the cartridge, its packaging, or both. Other identification components may also be used, including radio frequency identification devices (RFIDs), color coding, and other machine readable or human readable schemes.

Further, the CAEP 310 may have an associated reader or analogous circuitry to allow the automated analyzer 300 to detect the type of separation column 334 and automatically configure the automated analyzer 300. In this example, the automated analyzer 300 may automatically determine the appropriate BESs, electrophoresis conditions, and sample collection conditions for the targeted biomolecules based on type of separation column 334 that is present.

From the separation column 334, eluted fractions are carried by a tubing line 340 to one or more detectors 342. As mentioned with respect to FIG. 2 above, the detectors may include, for example, a fluorescent spectrophotometer, an ultraviolet spectrophotometer, a visible light spectrophotometer, a near infrared spectrophotometer, a refractive index detector, or any number of other suitable detection units. The detection unit is not limited to spectroscopic techniques and may use totally different techniques, for example, electrochemical detection techniques. The detector 342 may be connected to the CAEP 310 by control and signal lines 344. The control and signal lines 344 may carry power from the CAEP 310 to the detector 342 and signals from the detector 342 back to the CAEP 310. Using the signal from the detector 342, the CAEP 310 may control a sample collection system 346 through one or more control lines 348. The sample collection system 346 allows the solution flow from the detector 342 to be collected in any one of a number of sample tubes 350. Furthermore, the solution flow from the detector 342 may be sent to the waste container 327 through a tubing line 352 to allow materials coming off the column to be discarded.

The CAEP 310 may also be used to determine if the automated analyzer 300 needs servicing. For example, level detection lines 354 may connect the CAEP 310 to each solution reservoir 302 to determine if the solution is running low. Further, a level detection line 356 may also be connected to the waste container 327 to determine if the waste container 327 needs to be emptied. One of ordinary skill in the art will recognize that any number of additional configurations may be used to allow the CAEP 310 to determine the operational status of the automated analyzer 300.

Columns that may be Used in the Automated Analyzer

Any number of column configurations may be used in the automated analyzer 300 discussed with respect to FIG. 3, above. For example, one such column that may be used in an embodiment may include a separation column having a single elution and/or electrophoresis path, as discussed with respect to FIG. 4, below. To decrease the amount of solution required and to increase the speed of analysis, this configuration may be manufactured into a micro-fluidic device, as discussed with respect to FIG. 5. Another embodiment may incorporate multiple elution and electrophoresis paths, as discussed with respect to FIG. 6. The multiple paths may improve, for example, the servicing or flexibility of such a column, as discussed with respect to FIG. 7. Further, the columns discussed with respect to FIGS. 6 and 7 may have a somewhat different operational sequence and tubing connections to take advantage of the two dimensional nature of the column. For example, multiple tubing lines may be connected to facilitate simultaneous pumping or electrophoresis of materials through the cross channels 606.

Figure 4:
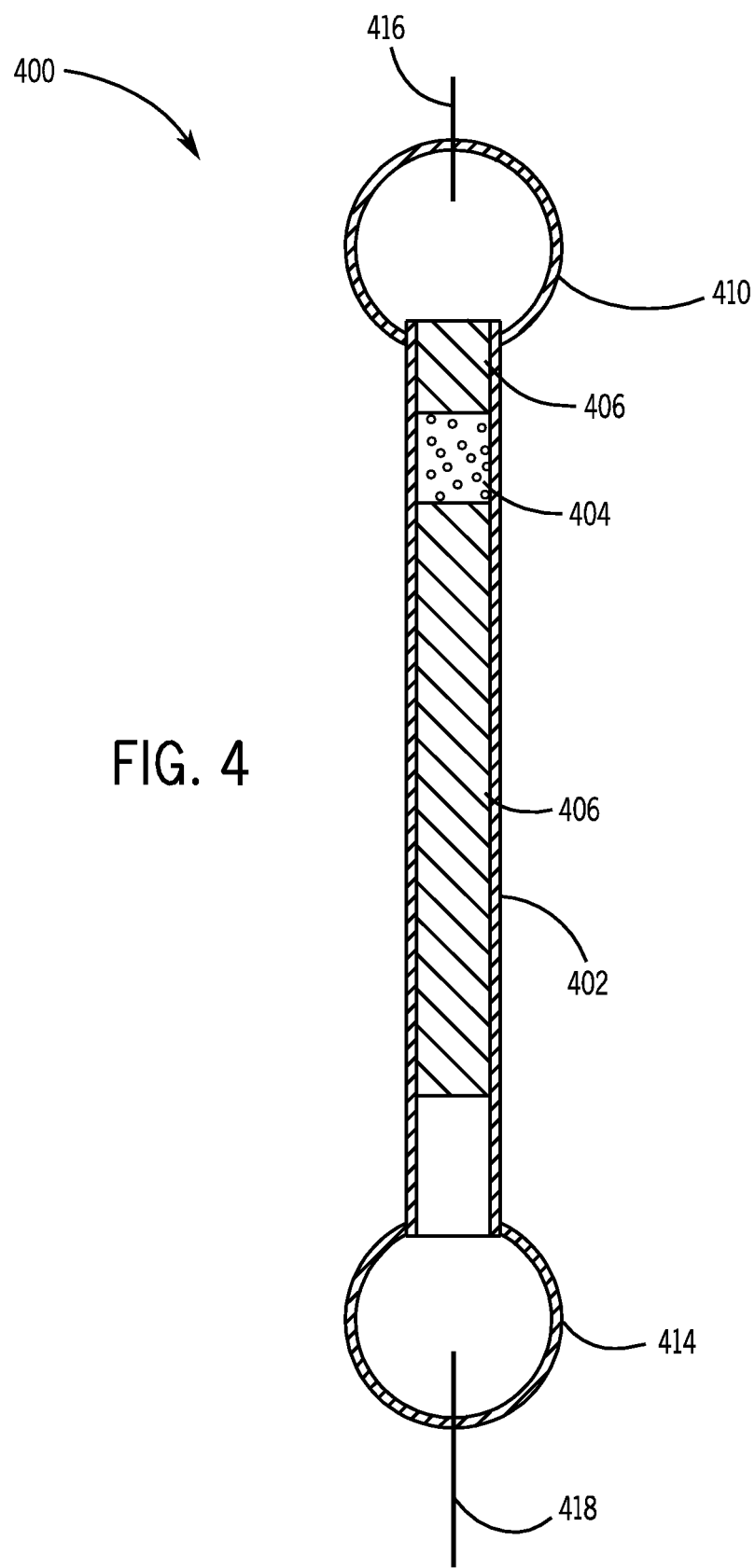
FIG. 4 is a cross sectional view of a purification column using elution techniques that may be used in an automated analyzer to isolate biomolecules, in accordance with an embodiment.

A single path separation column 400 that may be used in embodiments of the present techniques is illustrated by the cross sectional view shown in FIG. 4. In this column, a column body 402, for example, a glass tube, a metal tube, or a ceramic tube, may contain a substrate 404. Further, the tube may be a large diameter tube, e.g., about 4 or 5 mm wide, or may be a very small diameter tube, for example, a 0.25 mm capillary tube. The substrate 404 may reversibly adsorb molecules that have reacted with a BES more strongly than molecules that have not reacted with the BES. One of ordinary skill in the art will recognize that a separate substrate 404 may not be necessary, as the walls of the tube may function as the substrate 404, especially if the tube has a small diameter, such as a capillary tube. This may be more significant if the tube is made from a material commonly used as a substrate 404, e.g., glass. Materials that may be used as the substrate are discussed with respect to FIG. 1, above, and include, for example, glass fibers, silicone polymers, and anionic exchange resins, among others.

The substrate 404 may be surrounded by a matrix material 406, which may prevent the shifting or migration of the substrate 404 down the column body 402. The matrix material 406 may be, for example, an agarose, a polyacrylamide, a polyethylene oxide, a polyvinyl alcohol, a hydroxymethylcellulose, any combinations thereof, or any other suitable materials or combinations of material. Further, the matrix material 406 may act as a substrate 404, reversibly adsorbing the target biomolecules. If a matrix material 406 reversibly adsorbs the target biomolecules, a separate substrate 404 may not be needed. Further, if the tube is a capillary tube, for example, a glass capillary tube, a matrix material 406 may not be needed.

The column 400 may have a sample introduced through an inlet connection 410 at one end. In an embodiment, the inlet connection 410 may be a pressure fitting joined to a tubing line from a six-way valve 316, as discussed with respect to FIG. 3, above. In another embodiment, the inlet connection 410 may be a sample well, configured to accept the insertion of a sample. The separated components may be collected from an outlet connection 414 at the opposite end of the column. If the inlet connection 410 is a pressure fitting, the outlet connection 414 may generally be a pressure fitting, to allow for operation of the column 400 under a positive flow of solvent. However, if the inlet connection 410 is a sample well, the outlet connection 414 may generally also be a sample well.

Separation of the components introduced onto the column 400 may take place using solution flow, electrophoresis, or a combination of both to elute materials. If electrophoresis is used, either by itself or in combination with solution flow, electrodes may be attached at the ends of the column 400. For example, these electrodes may include a first electrode 416 attached to the inlet connection 410 and a second electrode 418 attached to the outlet connection 414. One of ordinary skill in the art will recognize that the electrical configuration of the electrodes 416 and 418 may depend on the target biomolecules. For example, in an embodiment, the first electrode 416 may be a ground wire and the second electrode 418 may be a high voltage positive wire. This arrangement of connections may generally be useful for the elution of anionic species from the column.

In an operation of the column 400, a sample that has been reacted with a BES, as discussed with respect to FIG. 1, may be introduced through the inlet connection 410. The sample may be flowed onto the column 400 by a continuous flow of solvent. Generally, the target biomolecules will be reversibly adsorbed onto the substrate 404. Contaminants may then be eluted from the column by electrophoresis, solvent flow, or a combination thereof. Once no further contaminants or residual BES is detected in eluate flowing from the column outlet 414, a release solution, as discussed with respect to FIG. 1, may be introduced into the column 400. In certain embodiments, the current may be switched off to allow the release agent to free the target biomolecules before attempting elution. In other embodiments, the current may be left on to enhance removal of the target biomolecules and prevent their re-adsorption onto the substrate 404. The eluate containing the target biomolecules may then be collected as it flows from the column outlet 414.

The column configuration discussed with respect to FIG. 4 may be implemented as a micro-fluidic device 500, as illustrated by the perspective view of FIG. 5. The device illustrated in FIG. 5 may be formed by cutting, etching, or forming a channel 502 into a base material 504. The channel 502 may be about 1 to about 10 mm wide. In certain embodiments, the channel may be about 1 mm wide, about 2 mm wide, about 3 mm wide, or about 4 mm wide. Other embodiments may use a larger channel, for example, about 15 mm wide. Further, the channel may be about 20 mm to about 100 mm in length. In embodiments, the channel may be about 40 mm, about 60 mm, about 80 mm, or about 100 mm in length. The base material 504 may be steel, glass, silicone elastomer, silicon, polyvinyl chloride (PVC), polyethylene terphthalate (PET), polyethylene (PE), polypropylene (PP), polymethylmethacrylate (PMMA), polycarbonate (PC), or any other suitable material. The base material should be resistant to the materials, solvents, and samples components used. Further, the base material interactions with the target biomolecules should be understood to prevent adhesion or degradation.

The micro-fluidic device 500 may be formed, for example, by injection molding, photographic etching, machining, or any other suitable technique. Once the base material 504 having the channel 502 is formed, the individual materials that may facilitate the separation may be inserted. Such materials may include a substrate 506 for reversibly adsorbing target biomolecules after reaction with a BES. Further, the micro-fluidic device 500 may also have a matrix material 508 added to the channel 502 to prevent the migration of the substrate 506. If electrophoresis is to be used for eluting materials, in addition to, or in place of solvent elution, a first electrode 510 may be connected to a sample inlet 512 and a second electrode 514 may be connected to an eluate outlet 516. The electrophoresis electrodes 510 and 514 may be placed in any location on the column, although they will generally bracket the substrate 506. The micro-fluidic device 500 may be enclosed in a cartridge for easy insertion into, and removal from, an analyzer, as discussed with respect to the separation column 334 in the automated analyzer 300. The cartridge may have an associated identification component, such as a bar code printed on the packaging or on the cartridge itself. Other identification components may also be used, including RFIDs, color coding, or other machine readable or human readable markings.

A pressure plate may be affixed over the micro-fluidic device 500 to allow the flow of solvent under pressure through the micro-fluidic device. Such a pressure plate may contain pressure fittings for the connection of tubing lines over the sample inlet 512 and eluate outlet 516. The pressure plate may also include connections for electrophoresis electrodes 510 and 514. The material used to form the pressure plate may be selected from the same materials used to form the base material 504 and may be the same or different than the base material.

Operation of the micro-fluidic device 500 is similar to that discussed with respect to FIG. 4. For example, a sample may be reacted with a BES and then introduced into the sample inlet 512, as indicated by reference numeral 518. The sample may be eluted through the column by solvent flow, electrophoresis, or both. The contaminants, including any excess BES, are washed from the micro-fluidic device 500 and may be tracked by analyzing the eluate from the eluate outlet 516. Once no further contaminants are detected, or after a sufficient time has passed, a release agent may be flowed through the micro-fluidic device 500 to free the target biomolecules from the substrate 506. The target biomolecules may then be eluted from the micro-fluidic device 500 and collected in the eluate.

The flow of eluate does not have to be contiguous, but may be separated into different paths for more effective isolation of target biomolecules or for the simultaneous isolation of different target biomolecules. For example, a device 600 that separates the eluate into different pathways is illustrated in FIG. 6. In this device 600, channels 602 are formed in a base material 604 using the techniques discussed with respect to FIG. 5. However, in this device 600, one or more cross channels 606 are formed across a main channel 608. The base material 604 may be selected from the materials discussed with respect to FIG. 5.

Substrates may be deposited at the intersection, e.g., fluidically coupled to, the cross channels 606 and the main channel 608 for the adsorption of target biomolecules. For example, in a device having two cross channels 606, two different substrate materials, each targeting different biomolecules, may be used. For example, the first substrate 610 may include paraffinic beads that are activated for the adsorption of protein molecules, while a second substrate 612 may have silica beads for the adsorption of nucleic acids. The substrates 610 and 612 may be held in place by the use of a matrix material 614, which may be used to keep the substrate materials 610 and 612 at the junctions of the cross channels 606 with the main channel 608.

The device may use solvent flow for the elution of materials from each substrate 610 and 612, or may use electrophoresis for the elution of materials in addition to or in place of the solvent elution. For examples, a first set of electrodes 616 may be located at the sample inlet 618 and the eluate outlet 620 of the main channel 608. In addition, a second set of electrodes 622 may be located across the cross channel 606 that intersects the first substrate 610 and a third set of electrodes 624 may be located across the cross channel 606 that intersects the second substrate 612. As for the micro-fluidic device 500 discussed with respect to FIG. 5, the device 600 may have a pressure plate including pressure fitting attached over the front surface.

The operation of the device 600 may is similar to the column 400 discussed with respect to FIG. 4. However, the cross channels 606 allow the simultaneous isolation of different target biomolecules. For example, during operation an aliquot of a sample may be reacted with a BES, after which the sample solution is flowed or eluted through the main channel 608 of the device 600, trapping a first set of target biomolecules on the first substrate 610. As the second substrate 612 targets different biomolecules, a second set of target biomolecules may be trapped the second substrate 612. After the target biomolecules are trapped on the substrates 610 and 612, contaminants, including excess BESs, may be flowed or eluted from the device 600 and removed from any of the main channel 608 or the cross channels 606. Once the contaminants have been removed, release agent may be flowed or eluted through each of the cross channels 606, and the target biomolecules may be isolated from the eluate outlets of each cross channel 606, as indicated by reference numeral 626.

The device 600 discussed with respect to FIG. 6 may be made more configurable by the addition of removable carriers for the substrates 610 and 612. For example, the device 700, illustrated in FIG. 7, has a first carrier 702 that may contain the first substrate 610 and a second carrier 704 that may contain the second substrate 612. The substrate carriers 702 and 704 may be substituted with carriers containing any number of different substrate materials, as discussed with respect to FIG. 1, above, and allow the device 700 to be configurable for different applications. As for the devices discussed above, the device 700 may have a pressure plate mounted over the front face to allow for the use of solvent under pressure.

Operation of the Automated Analyzer

Figure 8:
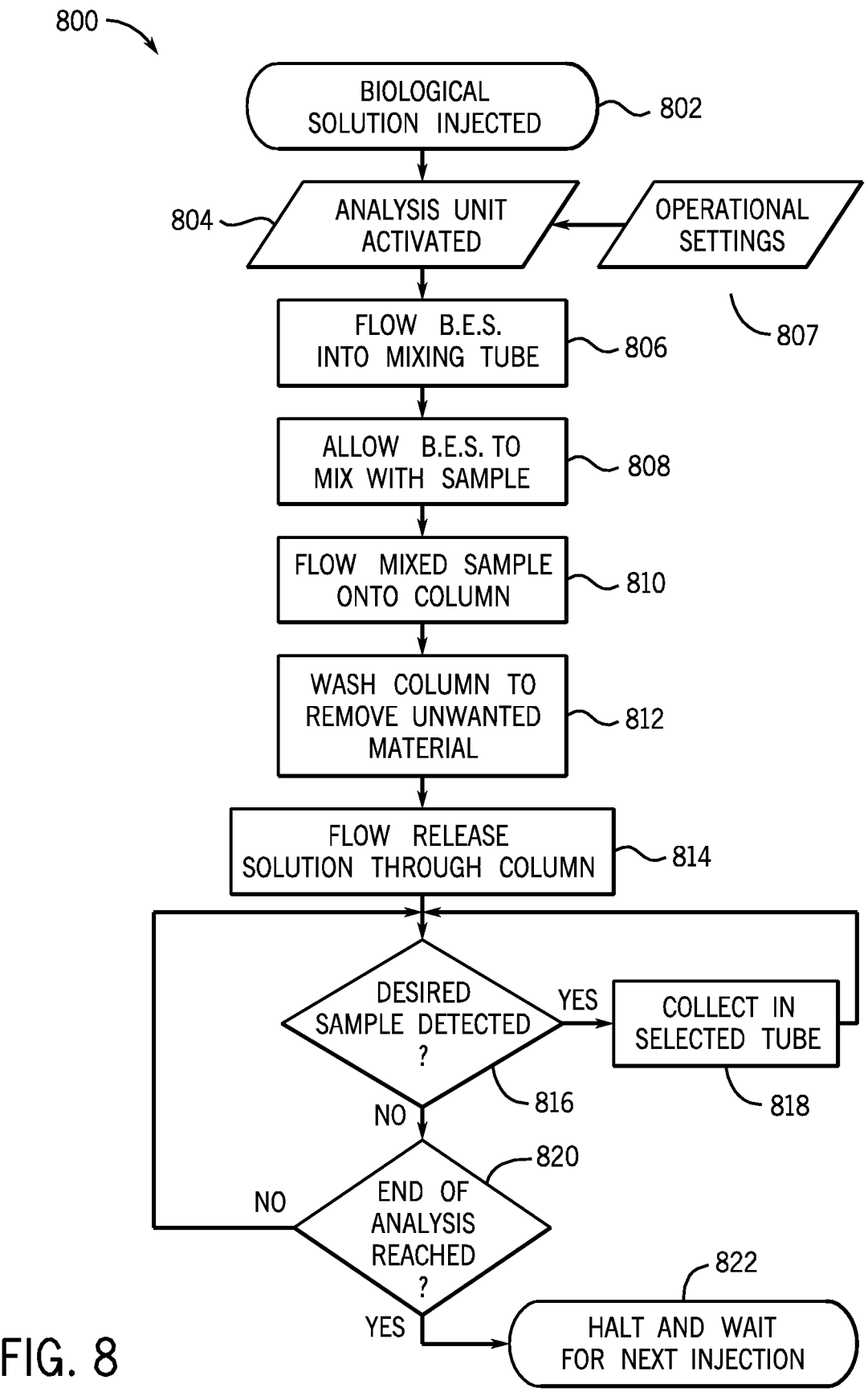
FIG. 8 is a flow chart illustrating a method for isolate a target biomolecule by an automated analyzer, in accordance with an embodiment.

The operation of the automatic analyzer 300, discussed with respect to FIG. 3, involves a number of automatically implemented process steps. One embodiment of such a method 800 may be illustrated in the flow chart of FIG. 8. The method 800 begins at block 802 with the injection of a sample at port 322 (FIG. 3). The user then activates the analysis (block 804) using operational parameters that were previously entered for the target biomolecules (block 807). For example, the operational parameters may include the type of target biomolecules, the collection start and stop events for the automatic collection of eluate, the solutions contained within the machine, and other parameters important to the separation and processing of the sample. One of ordinary skill in the art will recognize that the parameters may be any number of other relevant parameters, for example, the wavelengths to be scanned if the detector is a spectrophotometer.

Referring also to FIG. 3, after the analysis unit is activated, the CAEP 310 may rotate the six-way valve 316 and start a pump 304 to force (block 806) the appropriate BES into the reaction mixing tube 326 (block 806). Once a sufficient amount of the appropriate solution has been forced into the reaction mixing tube 326, the CAEP 310 may shut off the pump 304 to allow, for example, a reaction between the sample and the BES to take place (block 808). In embodiments, the reaction period may be, for example, about 15 seconds, about 30 seconds, about 1 minute, about 2 minutes, about 5 minutes, or longer. After the reaction has had sufficient time to react, the CAEP 310 may start the same or a different pump 304 to force the reacted sample solution through the six-way valve 316 and into a tubing line 330 (block 810), where the reacted sample solution may flow onto the separation column 334 (block 810). In the separation column 334, the target biomolecules may be reversibly adsorbed by a substrate, as previously discussed.

After the reacted sample solution has flowed onto the column, the CAEP 310 may activate a pump 304 (block 812) to force a wash solution onto the column (bock 812). The wash solution may be continuously flowed through the column to remove undesirable components. Alternatively, once an aliquot of the wash solution has been placed on the column, the solvent flow may be stopped and an electrophoresis current may be applied to the column to elute any undesirable components from the substrate. The eluate coming from the column may be monitored by the detector 342 to determine when the eluate is substantially free of contaminating species. One of ordinary skill in the art will recognize that the determination depends on a number of factors, including, for example, the desired purity level versus the amount of time and solution to be spent on the separation. Accordingly, a mixture of electrophoresis and solvent flow may provide good results, for example, by using a certain time period of electrophoresis without solvent flow to migrate impurities to the outlet of the column, then using a solvent flow to sweep the impurities out to the waste container 327.

Once the impurities have been removed, the CAEP 310 may activate a pump 304 to flow a release agent onto the column, as shown in block 814. As with the removal of impurities, removal of the target biomolecules may be entirely performed through solvent flow, or through electrophoresis, or through a combination of both. Again, a period of time during which only electrophoresis is occurring, followed by a restart of solvent flow may assist in purification of the target biomolecules.

While material is flowing from the column 334 through the detector 342, the CAEP 310 may monitor the signal (block 816) from the detector 342 to determine if target biomolecules are present. If target biomolecules are present, the CAEP 310 may switch the flow (block 818) in the sample collector 346 to collect the eluate flowing from the detector 342 into one or more sample vials 350. If none of the molecules of interest are detected, or if the signal from the detector 342 provides sufficient characterization of the target biomolecules, the CAEP 310 may discard the eluate to the waste container 327.

If target biomolecules are not detected in block 820, the method 800 determines if the end of the analysis is reached. If not, the method 800 resumes at block 816 and continues to analyze the eluate for the target biomolecules.

If the end of the analysis has been reached, the CAEP 310 may stop the analysis (block 822). At this point in the method, the CAEP 310 may perform any number of routine activities designed to report the status of the unit and the need for any servicing to the user. For example, the CAEP 310 may determine the level of the solutions in each solution reservoir 302, and inform the user if the level in any solution reservoir 302 is too low for another analysis. Further, the CAEP 310 may determine the level of the solution in the waste container 327 and inform the user if the level is too high.

User Operation of the Automated Analyzer

Figure 9:
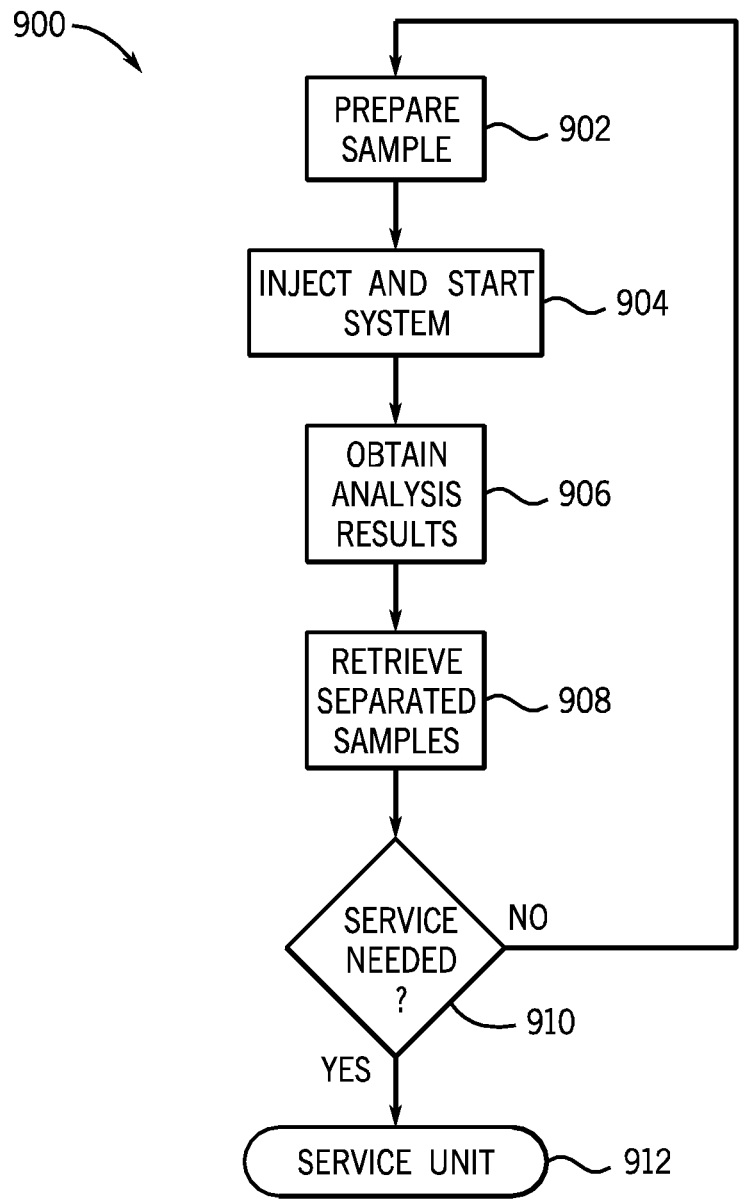
FIG. 9 is a flow chart illustrating the operation of an automated analyzer in isolating a target biomolecule, in accordance with an embodiment.

FIG. 9 is a flow chart that illustrates a method 900 that a user may follow when using the automated analyzer 300, as discussed with respect to FIG. 3. The method 900 begins at block 902 with sample preparation. The sample preparation involves any number of potential steps for collecting a sample and placing it in a condition for injection into the automated analyzer 300. For example, a cotton swab may be used to collect a sample from a surface in a public setting such as, for example, an airport, shopping mall, or other location. The cotton swab may then be placed into a mixing vessel, for example, a test tube, and mixed with an aqueous solution to rinse any biological components off of the swab and into the solution. The rinsate from the cotton swab may be pulled into a syringe. A syringe filter may then be attached to the syringe and the rinsate forced through the syringe filter to remove any solids. The solution does not necessarily need to be filtered before use. However, such filtration may decrease the servicing requirements for the automated analyzer 300.

One of ordinary skill in the art will recognize that any number of other solutions that contain biological molecules or sources of biological molecules may be used in embodiments of the present techniques. For example, laboratory cultures containing cells, bacteria cells, biological particles, and the like, may be used as the starting solutions for the techniques. Further, samples taken from a patient in a clinic environment, for example, blood samples, saliva samples, or other bodily fluids, may also be used in embodiments of the present techniques.

After the sample is prepared, the solution may be injected into the analyzer and the analyzer started (block 904). From that point on, the majority of the processing steps are performed within the analyzer as discussed with respect to FIG. 8. The user waits for the analysis to finish and, obtains the results (block 906) from the analysis. Further, the user may remove any samples of the isolated target biomolecules collected by the automated analyzer 300, as shown in block 908.

The samples of the isolated target biomolecules may be used in further applications and purification procedures. For example, the purified biological molecules or reaction products may be quantitatively or qualitatively analyzed for structure and function determination, identity testing or screening for particular properties of the isolated material. In one embodiment, for example, recombinant plasmid DNA may be extracted and isolated from the lysate generated during the exposure of bacterial cultures to the BES configured for this purpose. The recombinant plasmid DNA may then be tested by fragment analysis, sequencing, or sub-cloning. Furthermore the same bacterial culture may be exposed to other BESs configured to isolate and purify the protein products of the recombinant plasmid. Using this technique, the sequence structure of the gene in a recombinant plasmid may be directly associated with the function of that gene's protein product.

Furthermore, embodiments of the present techniques may be used to determine the identity, nature, or any alteration of the basic genotype of cells in a sample. This may be performed by extracting genomic DNA and isolating and purifying this DNA, using the techniques discussed above, prior to its use as a template in a PCR reaction. The techniques of the present disclosure may be used in any number of other applications, with or without further processing. For example, the present techniques may be used to isolate target biomolecules to determine cell identities, to correlate cell proteins with the genomic DNA that produced those proteins, or to identify other characteristics of the target biological molecules, perhaps using further biological transformations.

After the user has removed any desired samples from the unit, the user may determine whether the automated analyzer 300 needs to be serviced (block 910). For example, the levels in the solution reservoirs 302 and the waste container 327 may be checked. This check may be assisted by the unit itself, which may determine the current levels and inform the user if service is needed, as discussed with respect to FIG. 8. If no service is needed, the user may return to block 902 to start another analysis. If service is needed, the user may service the unit (block 912), for example, by filing any solution reservoir 302 that is low, or by emptying the waste container 127.

EXAMPLE

The micro-fluidic device 500, discussed with respect to FIG. 5, was tested to determine if the techniques discussed above could be used to isolate protein molecules from a sample solution containing both protein molecules and DNA molecules. The sample solution was mixed with BES B, which contained 0.1 N NaPO4, 0.1 M tris HCL and 20% glycerol.

The channel 502 in the micro-fluidic device 500 was about 2 mm across and about 40 mm in length. The substrate 506 consisted of GFX beads (available from GE Healthcare) in an agarose gel, and the matrix material 508 was a 1% agarose gel. The reacted sample was injected into the sample inlet 512, and about 100 V was applied across the channel 502. A total sample volume of less than about 2 microliters was required, with a binding time of less than about 5 minutes.

The DNA molecules were not bound to the substrate and were eluted from the column during the electrophoresis procedure. However, the protein molecules were bound to the beads and were visible in microscopic images, taken under ultraviolet light.

While only certain features of the invention have been illustrated and described herein, many modifications and changes will occur to those skilled in the art. For example, one of ordinary skill in the art will recognize that the method may be extend to large scale, automated analyses, such as may be used in a clinical or hospital setting. In this application, automated injectors and sample collectors may be interfaced with the automated analyzer to allow for the processing of larger sample numbers. It is, therefore, to be understood that the appended claims are intended to cover all such modifications and changes as fall within the true spirit of the invention.

What is claimed is:

1. A micro-fluidic device for isolating biological molecules from mixtures, comprising:
   a base material;
   a main channel formed in the base material;
   a cross channel formed in the base material, wherein the cross channel intersects the main channel;
   a substrate contained within a first carrier that is located at an intersection of the main channel and the cross channel and the substrate is capable of reversibly adsorbing via electrostatic interaction one or more biomolecules, wherein the first carrier is separate and distinct from the substrate and the first carrier is configured to be removably inserted at the intersection of the main channel with the cross channel;

one or more main channel electrophoresis connections on either side of the substrate disposed within the main channel; and one or more cross channel electrophoresis connections on either side of the substrate disposed within the cross channel.

2. The micro-fluidic device of claim 1, comprising a second cross channel intersecting the main channel.

3. The micro-fluidic device of claim 2, comprising a second substrate fluidically coupled with the main channel and the second cross channel.

4. The micro-fluidic device of claim 3, wherein the second substrate is contained within a second carrier configured to be removably inserted proximately to the intersection of the main channel with the second cross channel, and the second carrier is separate and distinct from the second substrate.

5. The micro-fluidic device of claim 1, wherein the micro-fluidic device is configured to elute molecules from the main channel, the cross channel, or both using solvent flow, electrophoresis, or combination thereof.

6. The micro-fluidic device of claim 1, wherein the micro-fluidic device is housed in a cartridge for insertion into and removal from an analyzer.

7. The micro-fluidic device of claim 6, wherein the cartridge has an identification component allowing automatic identification of the cartridge by the analyzer.

8. The micro-fluidic device of claim 1, wherein the substrate contained with the first carrier is configured to be inserted from directly above the intersection of the main channel with the cross channel.

* * * * *